(12) United States Patent
Lee et al.

(10) Patent No.: US 9,183,176 B2
(45) Date of Patent: Nov. 10, 2015

(54) METHOD AND APPARATUS FOR PROVIDING DRIVER-CUSTOMIZED VEHICLE SERVICE

(71) Applicant: Electronics and Telecommunications Research Institute, Daejeon (KR)

(72) Inventors: Shin-Kyung Lee, Daejeon (KR); Jeong-Woo Lee, Daejeon (KR); Doo-Seop Yun, Daejeon (KR); Oh-Cheon Kwon, Daejeon (KR); Hyun-Seo Oh, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 135 days.

(21) Appl. No.: 13/844,989

(22) Filed: Mar. 17, 2013

(65) Prior Publication Data

US 2013/0289798 A1 Oct. 31, 2013

(30) Foreign Application Priority Data

Apr. 25, 2012 (KR) ........................ 10-2012-0043396

(51) Int. Cl.
*G06F 17/00* (2006.01)
*G06F 7/00* (2006.01)
(Continued)

(52) U.S. Cl.
CPC ............... *G06F 17/00* (2013.01); *G01C 21/12* (2013.01); *G01C 21/36* (2013.01); *G06F 7/00* (2013.01); *G06F 19/3406* (2013.01); *G07C 5/085* (2013.01)

(58) Field of Classification Search
CPC ........... G06F 17/00; G06F 7/00; G01C 21/12; G01C 21/36
USPC ...................................... 701/1; 600/508, 483
See application file for complete search history.

(56) References Cited

U.S. PATENT DOCUMENTS

2008/0120025 A1* 5/2008 Naitou et al. ................. 701/207
2010/0049068 A1* 2/2010 Fuwamoto et al. ........... 600/509
(Continued)

FOREIGN PATENT DOCUMENTS

KR 10-2007-0093201 A 9/2007
KR 10-2010-0045923 A 5/2010
KR 10-2011-0127497 A 11/2011

OTHER PUBLICATIONS

Ahyoung Choi et al., "BioPebble: Stone-type physiological sensing device Supporting personalized physiological signal analysis", Korea HCI Association, 2008, pp. 13-18, vol. 1.
(Continued)

*Primary Examiner* — Fadey Jabr
*Assistant Examiner* — Yazan A Soofi
(74) *Attorney, Agent, or Firm* — Rabin & Berdo, P.C.

(57) ABSTRACT

The present invention relates to a method and apparatus for providing a driver-customized service. The present invention is configured to collect bio-signal information of a driver from a first sensor, collect current health condition information of the driver based on data stored in a health information DB, collect environmental condition information of an interior of a vehicle from a second sensor, collect environmental condition information of an exterior of the vehicle from a third sensor, generate a driving index based on the pieces of information collected from the first to third sensors and the health information DB, and perform a vehicle control operation corresponding to the driving index. Accordingly, the present invention not only enables the accident risk of drivers to be decreased, but also allows the drivers to drive their vehicles, which were considered to be only transportation means, in a safer and more comfortable environment.

13 Claims, 7 Drawing Sheets

(51) Int. Cl.
  *G01C 21/00* (2006.01)
  *G01C 21/12* (2006.01)
  *G01C 21/36* (2006.01)
  *G07C 5/08* (2006.01)
  *G06F 19/00* (2011.01)

(56) References Cited

U.S. PATENT DOCUMENTS

| | | | |
|---|---|---|---|
| 2010/0185101 A1* | 7/2010 | Sakai et al. | 600/483 |
| 2010/0207754 A1* | 8/2010 | Shostak et al. | 340/450 |
| 2011/0171080 A1* | 7/2011 | Lo | 422/186.3 |
| 2012/0078509 A1* | 3/2012 | Choi | 701/423 |
| 2012/0089299 A1* | 4/2012 | Breed | 701/36 |

OTHER PUBLICATIONS

Jeongah You et al., "Real-time life index web service using weather prediction", Korean Meteorological Society, 2001, pp. 383-385.

Joong-Kyung Ryu et al., "Context-aware based U-health Environment Information Service", Journal of Korea Contents Association, 2011, pp. 21-29.

* cited by examiner

METHOD AND APPARATUS FOR PROVIDING DRIVER-CUSTOMIZED VEHICLE SERVICE

CROSS REFERENCE TO RELATED APPLICATION

This application claims the benefit of Korean Patent Application No. 10-2012-0043396, filed on Apr. 25, 2012, which is hereby incorporated by reference in its entirety into this application.

BACKGROUND OF THE INVENTION

1. Technical Field

The present invention relates to a method and apparatus for providing a driver-customized service using information obtained by sensors provided in a vehicle, environmental information such as meteorological information, and medical information of a driver.

2. Description of the Related Art

There are conventional technologies, such as services based on a Ubiquitous Sensor Network (USN) which is merged with Information Technology (IT) or which uses a sensor network in medical fields, as in the case of Ubiquitous-health (U-health). In the field of telematics, services such as a remote fault diagnosis service or an emergency call (e-call: emergency relief) service have been provided.

However, such a conventional technology does not provide a personalized vehicle service suitable for a driver by utilizing not only information measured by the internal sensors of a vehicle, but also exterior environmental information such as meteorological information, and U-health information such as the prescription of the driver, when providing vehicle services to the driver.

That is, a conventional health management system and method having a database (DB)-based U-health nursing center (disclosed in Korean Unexamined Patent Publication No. 2010-0045923) disclose a method of providing a medical service to a user using a DB and real-time health condition information of a patient. However, this method is problematic in that it cannot be used while the driver is driving a vehicle. Further, the main purpose of a service, such as e-call, is to merely promptly collect and process fault information of a vehicle, and has a limitation in that it is difficult to apply such an e-call service to the provision of a service based on the current condition of the driver.

SUMMARY OF THE INVENTION

Accordingly, the present invention has been made keeping in mind the above problems occurring in the prior art, and an object of the present invention is to provide technology that provides a method for combining pieces of information from a plurality of domains (medical information, environmental information, information measured by internal and external sensors of the vehicle, etc.) and providing specialized and personalized application services suitable for each individual driver. In particular, the object of the present invention is to induce the creation of various types of vehicle services based on the present invention if merging between pieces of information required for individual persons has been implemented with the extension of IT technology.

That is, an object of the present invention is to provide a method for providing a driver-customized vehicle service using sensors installed inside and outside a vehicle, environmental information such as meteorological information, and the medical information of a driver.

In accordance with an aspect of the present invention to accomplish the above object, there is provided a method of providing a driver-customized service using a driver-customized vehicle control apparatus, including collecting bio-signal information of a driver from a first sensor, collecting current health condition information of the driver based on data stored in a health information database (DB), collecting environmental condition information of an interior of a vehicle from a second sensor, collecting environmental condition information of an exterior of the vehicle from a third sensor, and generating a driving index based on the pieces of information collected from the first to third sensors and the health information DB and performing a vehicle control operation corresponding to the generated driving index.

In accordance with another aspect of the present invention to accomplish the above object, there is provided an apparatus for providing a driver-customized service, including a first sensor for collecting bio-signal information of a driver, a health information database (DB) for storing data about current health condition information of the driver, a second sensor for collecting environmental condition information of an interior of a vehicle, a third sensor for collecting environmental condition information of an exterior of the vehicle, and a control unit for collecting pieces of information required to generate a driving index from the first to third sensors and the health information DB, generating the driving index, and performing a vehicle control operation corresponding to the generated driving index.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
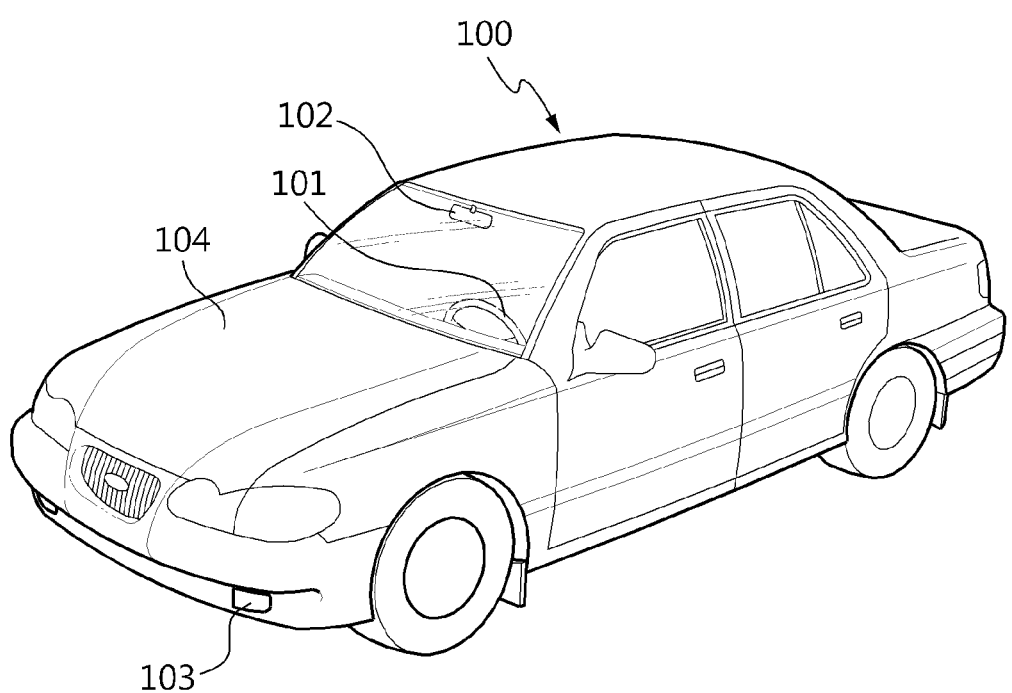
FIG. 1 is a diagram showing a vehicle capable of providing a driver-customized service according to an embodiment of the present invention.

Hereinafter, various embodiments of the present invention will be described in detail with reference to the attached drawings. Further, the terms "unit," "module," and "device" related to components used in the following description are merely assigned for the sake of simplicity of description of the present specification and may be used together and designed using hardware or software.

Further, embodiments of the present invention will be described in detail below with reference to the attached drawings and contents described in the drawings, but the present invention is not limited or restricted by the embodiments of the present invention.

FIG. 1 is a diagram showing a vehicle capable of providing a driver-customized service according to an embodiment of the present invention.

In accordance with this embodiment, a vehicle 100 may include therein a steering wheel 101 for collecting real-time bio-information of a driver, a vehicle interior environmental condition information collection sensor 102 for measuring cathon dioxide, cathon monoxide, and mites so as to obtain cleanliness status information of the interior of the vehicle, and a vehicle exterior environmental condition information collection sensor 103 for measuring the temperature, ultraviolet (UV) index, yellow dust level, pollen allergy level, rainfall, snowfall, etc. of the exterior of the vehicle.

The steering wheel 101 may measure bio-signals using body temperature, pulse (heart rate), and skin conductivity so as to collect the bio-information of the driver, may determine, based on a mean value in a normal condition, whether a current condition has deviated from the normal condition in the case of body temperature or pulse, and may determine, based on variations, that sweating is occurring in the case of skin conductivity. Further, in addition to the measurements, with the development of technology, various types of condition information of the driver (e.g., whether the driver is intoxicated or the like) are measured using the steering wheel 101, and may be used to provide the driver-customized service.

Further, the vehicle interior environmental condition information collection sensor 102 may separately measure and collect environmental condition information for three parts of the vehicle, that is, a lower part, a middle part, and an upper part, and may perform an operation of providing more detailed vehicle management information, such as automatic ventilation and vehicle interior washing, as well as providing a simple guideline for the replacement of an antibacterial filter or the like.

That is, by means of the above components, a driver-customized application service in which the driver himself or herself and the interior and exterior conditions of the vehicle are considered together may be provided.

Further, medical treatment information, such as an electronic prescription, is loaded from a health information database (DB) provided in the interior 104 of the vehicle, so that the current health condition of the driver may be considered in the provision of the driver-customized service.

That is, according to an embodiment, when a chronically allergic patient is driving a vehicle, the present invention may notify the driver of a simple maintenance guideline, such as for the replacement of an air filter, and a detailed vehicle management point, such as interior cleaning (floor or the entire interior space), based on the air measurement value of the interior of the vehicle, and may also induce the driver to wear a mask or may automatically ventilate the vehicle or block the inflow of external air in consideration of an external pollen level, a yellow dust level, or the like.

In accordance with another embodiment, the present invention may propose a bypass route which avoids an environment that may negatively influence the health of the driver even if the route is not a shortest route, upon selecting a route to a destination. Further, the present invention may generate driver-based vehicle driving and management indices (a safe driving index, a cleaning index, etc.) based on the pieces of collected information, and provide messages related to the indices to the driver.

In particular, when the safe driving index is not higher than that of a reference value at ordinary times, an emergency may inevitably occur while the driver is driving the vehicle. Accordingly, in preparation for this case, the present invention may support an emergency monitoring mode using a bio-handle and in-vehicle speech recognition. If it is determined that an emergency has occurred, an SOS message including Global Positioning System (GPS) information (location information) may be sent to an emergency contact number (a previously stored phone number) or, alternatively, a call to the emergency contact number may be automatically made.

Further, in accordance with an embodiment, if it is determined that an emergency has occurred, the present invention changes the mode of the vehicle to an automatic guidance mode, in which the vehicle automatically reduces its velocity to a constant level and determines a surrounding situation, thus inducing the vehicle to stop at the shoulder or on the roadside. Then, the present invention may perform control such that contact with a close fire station (by calling 119) and a close hospital can be made.

Figure 2:
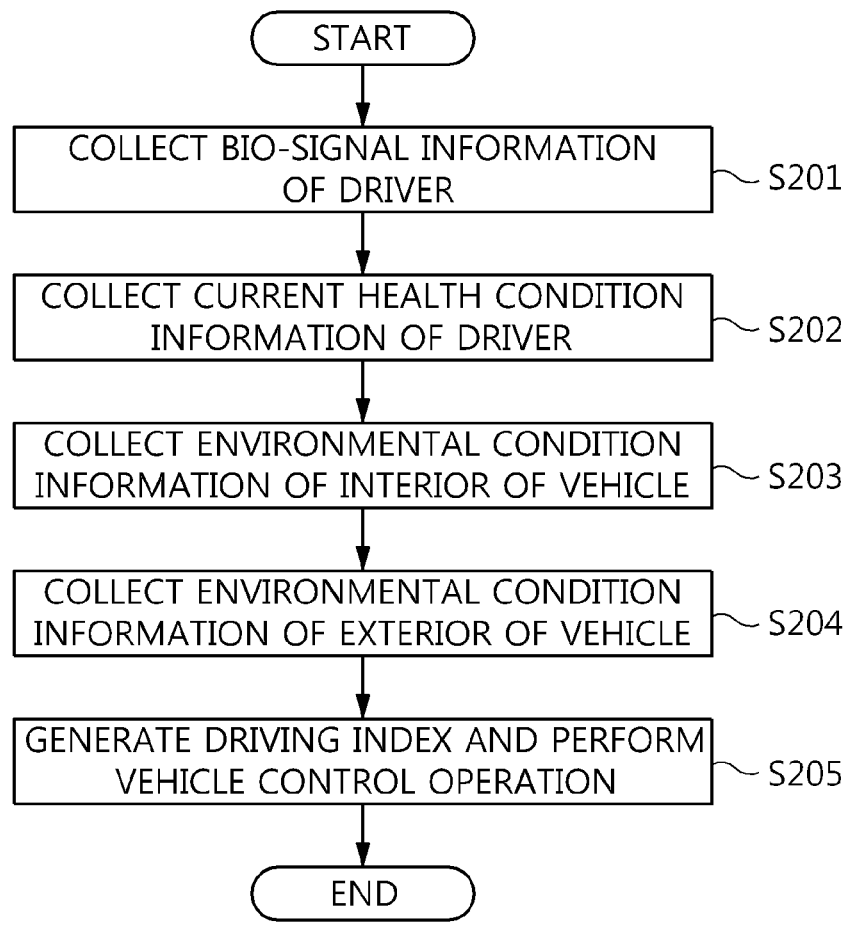
FIG. 2 is a flowchart showing a method of providing a driver-customized service according to an embodiment of the present invention.

FIG. 2 is a flowchart showing a method of providing a driver-customized service according to an embodiment of the present invention.

An apparatus for proving a driver-customized service may provide the service to a driver using the following steps.

First, the bio-signal information of the driver is collected at step S201.

In accordance with an embodiment, the bio-signal information of the driver may be collected from a first sensor. The first sensor may include a bio-signal information collection sensor mounted on the steering wheel of the vehicle and configured to collect the bio-information of the driver in real time.

Next, the current health (physical) condition information of the driver is collected at step S202.

In accordance with an embodiment, the current health condition information of the driver may be collected based on data stored in a heath information DB provided in the interior of the vehicle by searching the health information DB.

In accordance with another embodiment, the health information DB may be stored in an external system for providing health information, and the vehicle may receive the medical information of the driver stored in the health information DB stored in the external system over a network, thus collecting the current health condition information of the driver.

Further, the current health condition information of the driver may include medical treatment information, such as an electronic prescription.

Next, the environmental condition information of the interior of the vehicle is collected at step S203.

In accordance with an embodiment, the environmental condition information of the interior of the vehicle may be collected from a second sensor. The second sensor may correspond to a vehicle interior environmental condition information collection sensor, and may separately measure and collect the environmental condition information of the vehicle for three parts of the vehicle, that is, a lower part, a middle part, and an upper part. Therefore, it is possible to perform more exact measurements and provide a more useful service.

Next, the environmental condition information of the exterior of the vehicle is collected at step S204.

In accordance with an embodiment, the environmental condition information of the exterior of the vehicle may be collected from a third sensor. The third sensor may correspond to a vehicle exterior environmental condition information collection sensor and may measure the temperature, UV index, yellow dust level, pollen allergy level, rainfall, snowfall, etc. of the exterior of the vehicle.

Further, upon collecting the pieces of measurement information, the third sensor may receive meteorological information or related environmental information that may most influence the driving of the vehicle from an environmental information provision server over the network, and may collect the environmental condition information of the exterior of the vehicle.

Next, an operation of generating a driving index and controlling the vehicle is performed based on the pieces of collected information at step S205.

That is, the driving index is generated based on the pieces of information collected from the first to third sensors and the health information DB, and a vehicle control operation corresponding to the generated driving index is performed.

The driving index may include a safe driving index and a cleaning index, and may be generated based on a preset calculation criterion. This will be described in detail later with reference to FIG. 4.

Further, the vehicle control operation may include an operation of providing a specific message to the driver in voice or text, an operation of changing a mode to a driving mode in which the condition of the driver is monitored, an operation of changing the mode to a driving mode in which the vehicle safely stops, and operations of automatically sending a text message and making a call.

Figure 3:
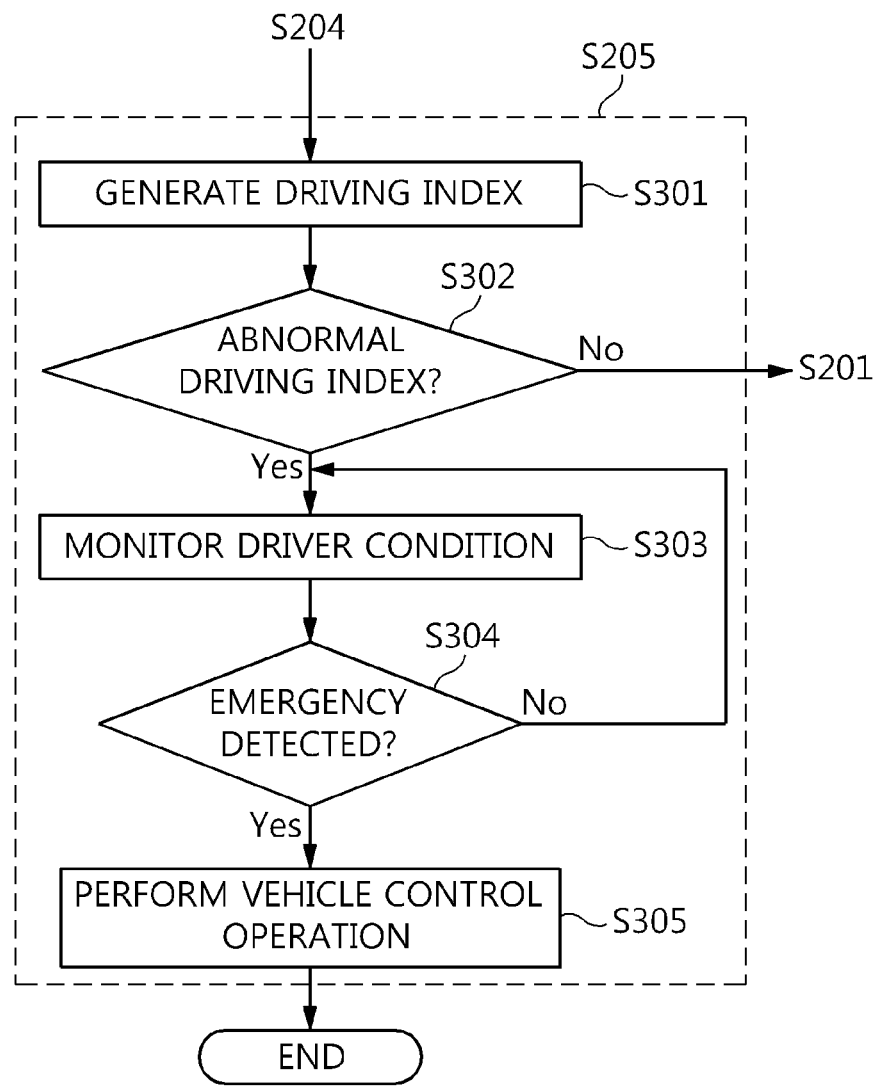
FIG. 3 is a flowchart showing the step of generating a driving index and performing a vehicle control operation shown in FIG. 2 in detail.

FIG. 3 is a flowchart showing the step of generating a driving index and performing a vehicle control operation shown in FIG. 2 in detail.

In accordance with an embodiment, in the driver-customized service provision apparatus, if pieces of information have been collected from the first to third sensors and the health information DB, a driving index may be generated based on the collected information at step S301, and it is determined whether the generated driving index falls within an abnormal range at step S302.

Figure 4:
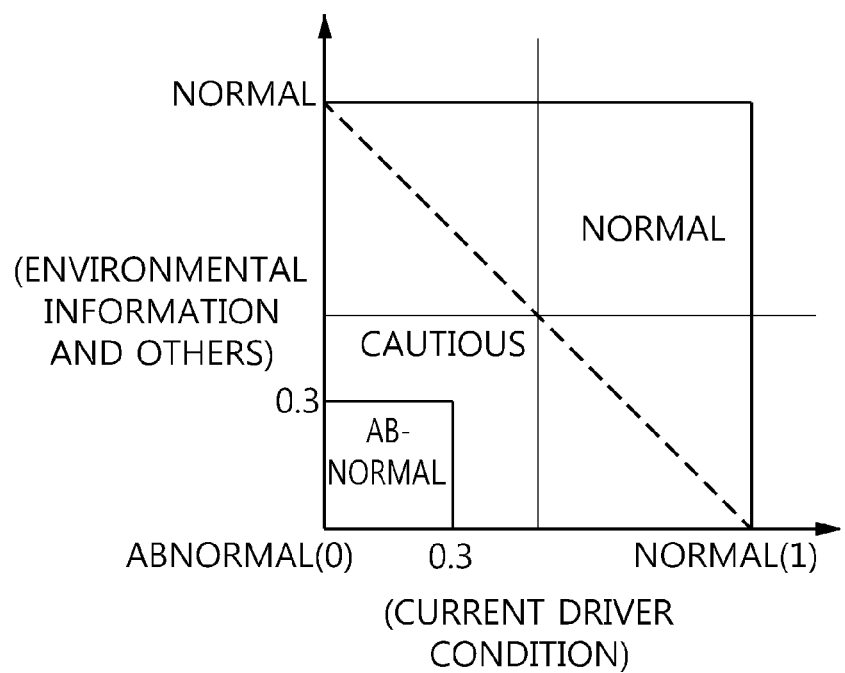
FIGS. 4 and 5 are diagrams showing graphs required to determine whether a driving index falls within a normal range according to an embodiment of the present invention.
Figure 5:
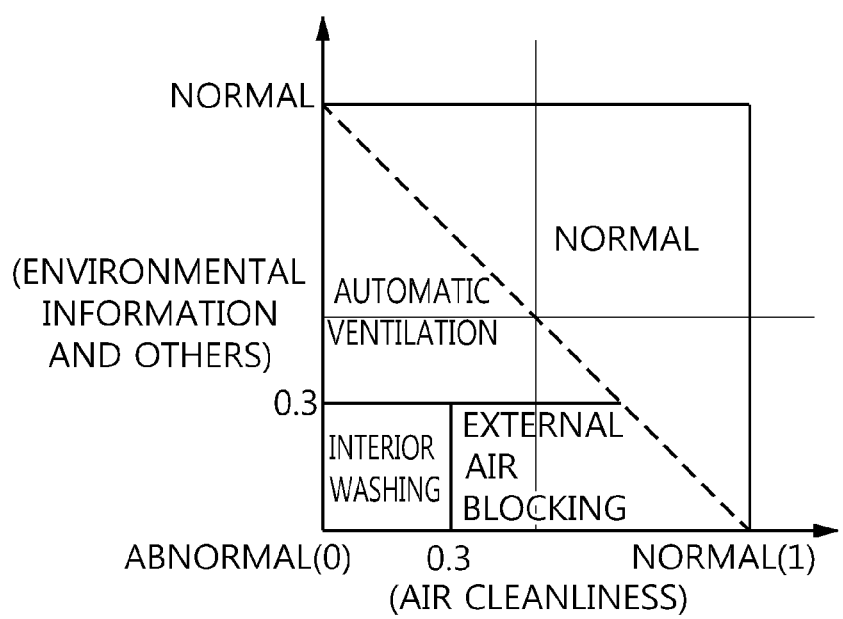
Figure 6:
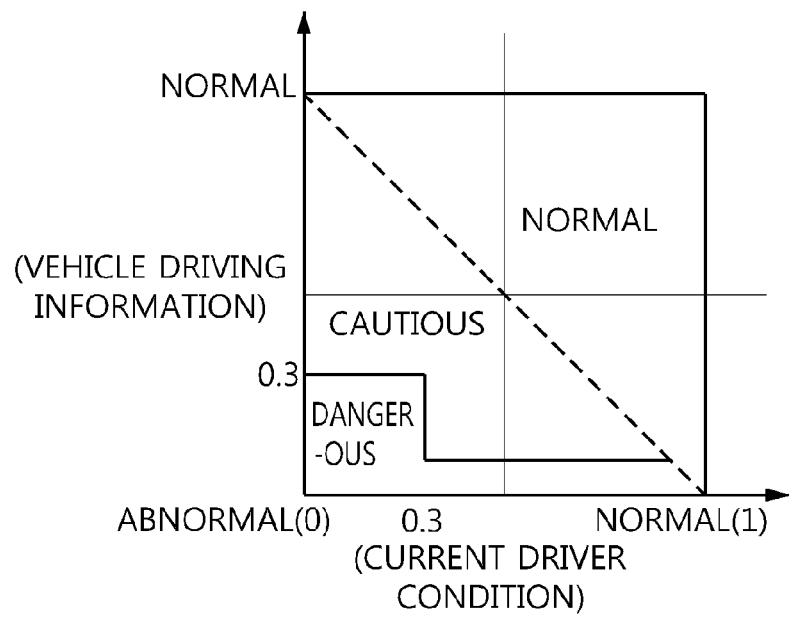
FIG. 6 is a diagram showing a graph required to determine the occurrence of an emergency according to an embodiment of the present invention.

That is, the driver-customized service provision apparatus may store information about the normal range of the driving index and then determine whether the driving index is normal or abnormal. Graphs required to determine whether the driving index is normal are shown in FIGS. 4 to 6.

If, as a result of the determination, the driving index falls within the normal range, the process returns to the step of collecting pieces of bio-signal information of the driver, and may re-collect pieces of information from the first to third sensors and the health information DB and again generate a driving index.

In contrast, if the driving index falls within an abnormal range, the condition of the driver is monitored in real time at step S303, and an emergency may be detected at step S304.

In accordance with an embodiment, the driver-customized service provision apparatus may analyze vehicle information collected from an in-vehicle network and the voice or facial expressions of the driver located inside the vehicle, and may then collect information required to detect an emergency.

Therefore, when an emergency is detected, a vehicle control operation is performed to provide a driver-customized service at step S305.

That is, when the condition of the driver is deteriorated to such an extent as to negatively influence driving during real-time monitoring, or when an emergency is detected through vehicle information (velocity, a steering angle, an accelerator pedal, etc.) collected from the in-vehicle network, speech recognition, or facial expression recognition, a service similar to that of emergency relief may be provided.

For example, an SOS message including GPS information (location information) may be sent to an emergency contact number (a previously stored phone number), or an emergency call may be made according to the priority. Further, the mode is changed to an automatic guidance mode in which the vehicle determines a surrounding situation and is induced to stop at the shoulder or on the roadside while automatically reducing its velocity to a constant level. Thereafter, a service, similar to an emergency relief, may be provided by making contact with a close fire station (by calling 119) and a close hospital.

FIGS. 4 and 5 are diagrams showing graphs required to determine whether a driving index falls within a normal range according to embodiments of the present invention.

In accordance with an embodiment, the driver-customized service provision apparatus may collect and combine pieces of information for respective domains (medical information, environmental information, sensor information, etc.), and may calculate various indices in consideration of not only the health condition of the driver, but also correlations between the pieces of information of the interior and exterior of the vehicle.

These indices are basic indices required to provide a vehicle service suitable for each individual driver, and may include a cleaning index required to guide the driver to detailed vehicle management in relation to whether ventilation is merely required or whether the washing of the interior of the vehicle is required by individually measuring air cleanliness in the upper, middle, and lower parts of the vehicle, or the safe driving index of the driver that most influences driving. That is, as is also illustrated in FIGS. 4-6, the driving index is a normalized value of multiple dimensions, each dimension corresponding to one of the bio-signal information of the driver, the health condition information of the driver, the interior environmental condition information of the vehicle and the exterior environmental condition information of the vehicle.

That is, the determination of conditions based on the safe driving index may be performed based on the value of current driver condition information (a value ranging from 0 to 1, 0: abnormal, 1: normal) which is obtained by the sensor for collecting the bio-signal of the driver, and the value of exterior environmental information (a value ranging from 0 to 1, 0: bad weather, 1: fine weather) which influences driving, such as snowfall and rainfall.

Further, as other situations, personal health information (health examination information or prescription information) may be applied as weights and then calculated.

Therefore, the driver-customized service provision apparatus may store the graph shown in FIG. 4 and may determine whether the driving index is normal or abnormal, based on the pieces of collected information.

Furthermore, the determination of conditions based on the cleaning index may be performed such that, on the basis of air measurement information (a value ranging from 0 to 1, 0: abnormal, 1: normal), when air cleanliness information is a value (0.3 to 0.7) requiring caution, automatic ventilation may be induced. However, when the value of the current condition information obtained through environmental information or the steering wheel is close to an abnormal value, determination may be performed, as shown in FIG. 5, so that the driver is recommended to wash the interior of the vehicle while blocking the inflow of external air without conducting ventilation.

FIG. 6 is a diagram showing a graph required to determine the occurrence of an emergency according to an embodiment of the present invention.

In accordance with an embodiment, with reference to the graph shown in FIG. 6, the driver-customized service provision apparatus may detect an emergency by analyzing vehicle information collected from the in-vehicle network and the voice or facial expressions of the driver located in the vehicle.

That is, a dangerous condition may be calculated based on current driver condition information (a value ranging from 0 to 1, 0: abnormal, 1: normal) which is obtained by the sensor for collecting the bio-signal of the driver, and vehicle information (a value ranging from 0 to 1, 0: abnormal driving, 1: normal driving), such as velocity, a steering angle, or an accelerator pedal, which is collected from the in-vehicle network.

Figure 7:
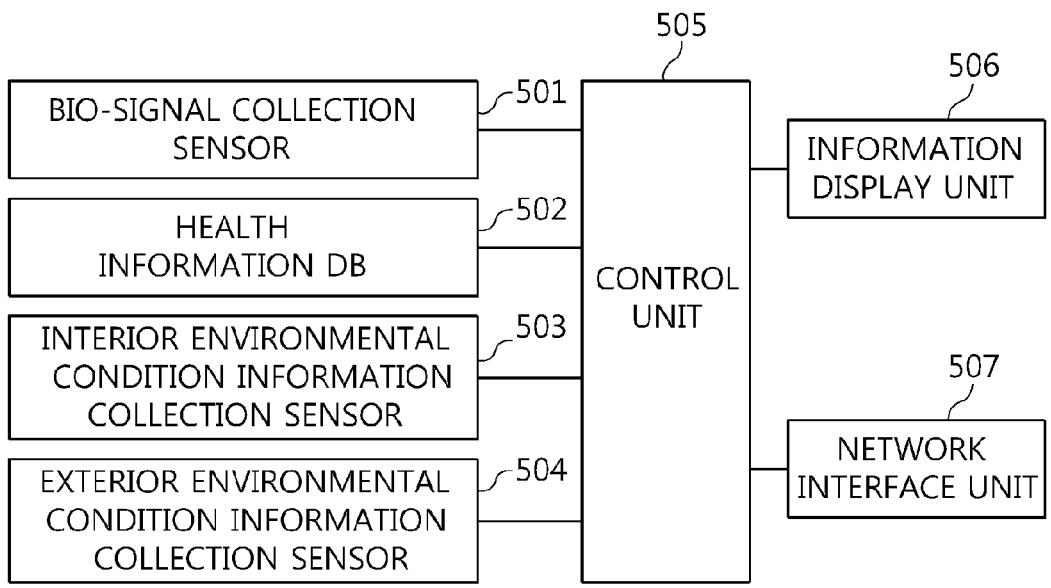
FIG. 7 is a block diagram showing the configuration of an apparatus for providing a driver-customized service according to an embodiment of the present invention.

FIG. 7 is a block diagram showing the configuration of an apparatus for providing a driver-customized service according to an embodiment of the present invention.

In accordance with an embodiment, the driver-customized service provision apparatus includes a bio-signal collection sensor 501, a health information DB 502, an interior environmental condition information collection sensor 503, an exterior environmental condition information collection sensor 504, a control unit 505, an information display unit 506, and a network interface unit 507.

The bio-signal collection sensor 501 may include a bio-signal information collection sensor mounted on the steering wheel of the vehicle and configured to collect the bio-information of the driver in real time.

In accordance with an embodiment, the health information DB 502 is a health information DB provided in the interior of the vehicle, and allows the current health condition information of the driver to be collected based on the data stored in the health information DB.

Further, in another embodiment, the health information DB 502 may include a DB for receiving required information from an external system that provides health information over the network, and storing the required information. Furthermore, the health condition information may include medical treatment information, such as an electronic prescription.

The interior environmental condition information collection sensor 503 may separately measure and collect environmental condition information for three parts of the vehicle, that is, a lower part, a middle part, and an upper part. Therefore, more exact measurements may be performed and a more useful service may be provided. Further, the interior environmental condition information collection sensor 503 may include an air cleanliness information sensor for checking the air condition of the interior of the vehicle.

The exterior environmental condition information collection sensor 504 may measure the temperature, UV index, yellow dust level, pollen allergy level, rainfall, snowfall, etc. of the exterior of the vehicle. In accordance with an embodiment, the sensor 504 may receive meteorological information or related environmental information which may most influence the driving of the vehicle from the environmental information provision server over the network, and may collect the environmental condition information of the exterior of the vehicle.

The control unit 505 may collect pieces of information required to generate a driving index from the sensors and the health information DB, generate the driving index, and perform a vehicle control operation corresponding to the generated driving index.

Further, the control unit 505 determines whether the driving index generated based on the pieces of collected information falls within a normal range. If it is determined that the generated driving index does not fall within the normal range, the control unit 505 monitors the condition of the driver in real time, and may perform the vehicle control operation if an emergency is detected in the monitored driver condition information.

Furthermore, if an emergency has not been detected for a predetermined period of time, the control unit 505 may perform control such that pieces of information are re-collected from the sensors and the health information DB and a driving index is generated again.

That is, the control unit 505 may generate a driving index that is basic data which not only enables the health information of the driver and the interior/exterior condition information of the vehicle to be inquired about, but also enables a vehicle service suitable for each individual driver to be provided in consideration of correlations between the pieces of information. For example, existing medical information enables only the health condition of the driver to be monitored. However, if correlations between the health condition information, the exterior environmental information, and interior air measurement information are taken into consideration, it is possible to notify a chronically allergic patient or the like of a bypass route in which an environment avoiding a condition negatively influencing the health of the driver is considered, rather than a shortest route, to provide an automatic ventilation service or the like by adjusting the open level of the window of a driver's seat, a passenger's seat, or rear seats, or to automatically block the inflow of external air in spring in which there is a large amount of pollen.

The information display unit 506 may display a message including contents of a driver-customized vehicle service into which the current health condition of the driver, an exterior meteorological condition, internal temperature, air cleanliness status, etc. are incorporated, and then provide information to the user.

The network interface unit 507 may receive required information from an external system which provides U-health information, such as an electronic prescription, or health examination information.

Figure 8:
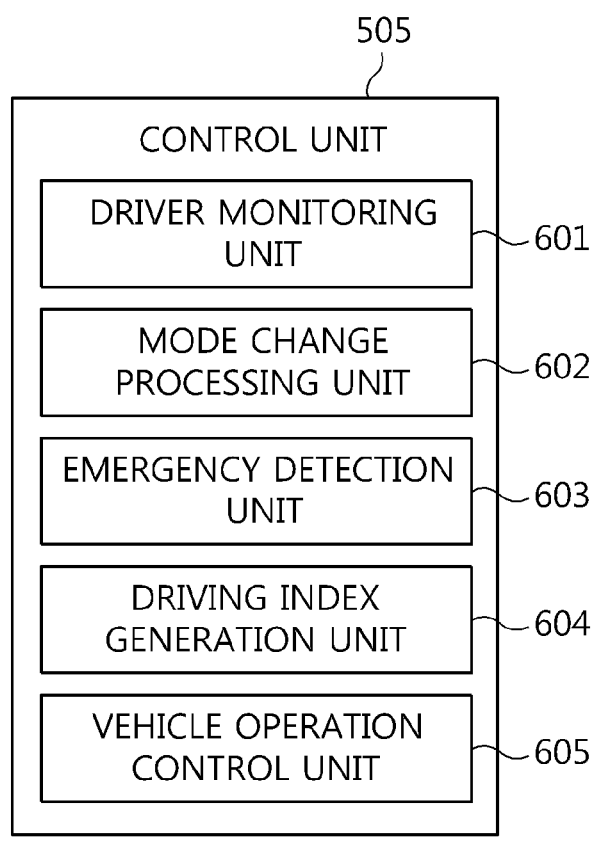
FIG. 8 is a block diagram showing the configuration of a control unit included in the driver-customized service provision apparatus according to an embodiment of the present invention in detail.

FIG. 8 is a block diagram showing the configuration of the control unit included in the driver-customized service provision apparatus according to an embodiment of the present invention in detail.

In accordance with an embodiment, the control unit 505 may include a driver monitoring unit 601, a mode change processing unit 602, an emergency detection unit 603, a driving index generation unit 604, and a vehicle operation control unit 605.

The driving index generation unit 604 may generate a driving index based on the pieces of information collected from the sensors and the DB, and allow the driver monitoring unit 601 to perform a monitoring operation if the generated driving index falls within an abnormal range.

The driver monitoring unit 601 may monitor the condition of the driver in real time.

That is, the driver monitoring unit 601 may monitor information collected from the steering wheel, vehicle information collected from the internal sensors of the vehicle, and information about voice or facial expressions in the vehicle. The emergency detection unit 603 may detect an emergency based on the monitored information. A criterion for the determination of an emergency has been described above with reference to FIG. 6.

Further, if it is determined that no special abnormality is detected after real-time monitoring has been maintained for a predetermined period of time, the emergency detection unit 603 may transmit a control signal required to recalculate the driving and management indices of each driver based on various pieces of domain information to the vehicle operation control unit 605.

The mode change processing unit 602 may perform control so as to perform an operation of changing the mode of the vehicle to the driver monitoring mode if the driving index falls within the abnormal range, and an operation of changing the mode of the vehicle to an automatic guidance mode in which the vehicle may stop in a safe place if an emergency has been detected.

The vehicle operation control unit 605 may control other components of the control unit so that a vehicle control operation corresponding to the driving index generated by the driving index generation unit 604 is performed.

As described above, a driver-customized vehicle service according to the present invention not only enables the accident risk of drivers to be decreased, but also allows the drivers to drive their own vehicles, which were considered to be only transportation means, in a safer and more comfortable environment.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. These modifications should not be understood separately from the technical spirit or prospect of the present invention.

What is claimed is:

1. A method of providing a driver-customized service for a driver of a vehicle using a driver-customized vehicle control apparatus that includes first, second and third sensors and a health information database (DB), comprising:
    collecting bio-signal information of the driver from the first sensor;
    collecting current health condition information of the driver based on data stored in the health information DB;
    collecting environmental condition information of an interior of the vehicle from the second sensor;
    collecting environmental condition information of an exterior of the vehicle from the third sensor;
    generating a driving index based on pieces of information collected from the first, second and third sensors and the health information DB, the driving index being a normalized value of multiple dimensions, each dimension corresponding to one of the bio-signal information of the driver, the health condition information of the driver, the interior environmental condition information of the vehicle and the exterior environmental condition information of the vehicle, the driving index including
        a safe driving index that is a two-dimensional (2D) value with the two dimensions respectively corresponding to the bio-signal information of the driver and the exterior environmental condition information of the vehicle, the safe driving index being configured to be adjustable based on the current health condition information, and
        a cleaning index that is a 2D value with the two dimensions respectively corresponding to the interior and exterior environmental condition information of the vehicle; and
    performing a vehicle control operation, including at least one of notifying the driver or a third party and changing a driving mode of the vehicle, in accordance with the generated driving index.

2. The method of claim 1, further comprising receiving, by the health information DB from an external system for providing health information, medical information of the driver stored in the external system over a network, and storing the medical information.

3. The method of claim 1, wherein performing the vehicle control operation comprises:
    determining whether the generated driving index falls within a normal range; and
    upon determining that the generated driving index is out of the normal range,
        monitoring a condition of the driver in real time, and
        performing the vehicle control operation upon detecting an emergency based on the monitored driver condition.

4. The method of claim 1, wherein the vehicle control operation is an operation of sending a message or making a call to a preset contact number.

5. The method of claim 1, wherein the first sensor is mounted on a steering wheel of the vehicle and configured to collect the bio-information of the driver in real time.

6. The method of claim 1, wherein the second sensor is an air cleanliness collection sensor for separately measuring cleanliness information of the interior of the vehicle for respective lower, middle, and upper parts of the interior of the vehicle.

7. An apparatus for providing a driver-customized service for a driver of a vehicle, comprising:
    a first sensor for collecting bio-signal information of the driver;
    a health information database (DB) for storing data about current health condition information of the driver;
    a second sensor for collecting environmental condition information of an interior of the vehicle;
    a third sensor for collecting environmental condition information of an exterior of the vehicle; and
    a control unit for
        collecting pieces of information required to generate a driving index from the first, second and third sensors and the health information DB, and generating the driving index, the driving index being a normalized value of multiple dimensions, each dimension corresponding to one of the bio-signal information of the driver, the health condition information of the driver, the interior environmental condition information of the vehicle and the exterior environmental condition information of the vehicle, the driving index including
            a safe driving index that is a two-dimensional (2D) value with the two dimensions respectively corresponding to the bio-signal information of the driver and the exterior environmental condition information of the vehicle, the safe driving index being configured to be adjustable based on the current health condition information, and
            a cleaning index that is a 2D value with the two dimensions respectively corresponding to the interior and exterior environmental condition information of the vehicle; and performing a vehicle control operation corresponding to the generated driving index.

8. The apparatus of claim 7, wherein the health information DB receives medical information of the driver from an external system for providing health information over a network, and stores the medical information.

9. The apparatus of claim 7, wherein the control unit
is configured to determine whether the generated driving index falls within a normal range, and
is configured to, upon determining that the generated driving index is out of the normal range, monitor a condition of the driver in real time, and perform the vehicle control operation upon detecting an emergency from the monitored driver condition.

10. The apparatus of claim 7, wherein the vehicle control operation is an operation of changing a driving mode of the vehicle.

11. The apparatus of claim 7, wherein the vehicle control operation is an operation of sending a message or making a call to a preset contact number.

12. The apparatus of claim 7, wherein the first sensor is mounted on a steering wheel of the vehicle and configured to collect the bio-information of the driver in real time.

13. The apparatus of claim 7, wherein the second sensor is an air cleanliness collection sensor for separately measuring cleanliness information of the interior of the vehicle for respective lower, middle, and upper parts of the interior of the vehicle.

* * * * *